United States Patent
Akita et al.

(10) Patent No.: US 6,171,272 B1
(45) Date of Patent: Jan. 9, 2001

(54) SHORT LEG BRACE

(75) Inventors: Yoshiyuki Akita, Saitama; Sumiko Yamamoto; Shigeru Kubo, both of Tokyo; Hideo Kawai, Ibaraki; Masahiko Ebina; Takeo Hayashi, both of Tokyo; Yoshiharu Kitamura, Kanagawa, all of (JP)

(73) Assignee: NHK Spring Co., Ltd., Yokohama (JP)

( * ) Notice: Under 35 U.S.C. 154(b), the term of this patent shall be extended for 0 days.

(21) Appl. No.: 09/051,526

(22) PCT Filed: Oct. 9, 1996

(86) PCT No.: PCT/JP96/02930

§ 371 Date: Apr. 10, 1998

§ 102(e) Date: Apr. 10, 1998

(87) PCT Pub. No.: WO97/13487

PCT Pub. Date: Apr. 17, 1997

(30) Foreign Application Priority Data

Oct. 12, 1995 (JP) .................................................. 7-290402

(51) Int. Cl.[7] ........................................................ A61F 5/00
(52) U.S. Cl. ................................................ 602/28; 602/27
(58) Field of Search .................................. 602/27–29, 23, 602/26, 16, 21; 128/882

(56) References Cited

U.S. PATENT DOCUMENTS 4,955,370 * 9/1990 Pettine .................................... 602/78

FOREIGN PATENT DOCUMENTS 40-26554  9/1965 (JP) .
61-16173  4/1986 (JP) .

OTHER PUBLICATIONS

Ogishima, Hideo. "Brace, Self–Help Device and Wheel Chair".

* cited by examiner

*Primary Examiner*—Mickey Yu
*Assistant Examiner*—Denise Pothier
(74) *Attorney, Agent, or Firm*—Skjerven Morrill MacPherson LLP; George Wolken, Jr.

(57) ABSTRACT

A short leg brace which is composed of a foot mount and a calf splint pivotably attached to each other so as to allow plantar and dorsal flexions and which is provided with a compression spring between the splint and the heel portion of the mount for elastically hindering the plantar flexion.

7 Claims, 7 Drawing Sheets

(A) (HC) (FF)

(B) (HC) (FF)

(C) (HC) (FF)

SHORT LEG BRACE

TECHNICAL FIELD

The present invention relates to a short leg brace which is used by patients who need support to their ankle joint when they walk.

BACKGROUND OF THE INVENTION

A short leg brace such as shown in FIG. 5 is conventionally known as a support used by patients who, due to paralysis resulting from cerebral hemorrhage or cerebral thrombosis or due to hemiplegia resulting from an accident, cannot move their ankle joint as they intend.

This conventional short leg brace is made of relatively rigid synthetic resin material, and comprises a foot mount 10A for supporting the foot sole S and a calf splint 20A which is to be set along the calf C, wherein the foot mount 10A and the calf splint 20A are molded integrally. With the foot mount 10A placed under the foot and the calf splint 20A set along the calf C, the short leg brace is secured by means of fixing bands 50. Thus, the short leg braces of this type stabilize the leg and the foot sole in an approximately right angle (so that the ankle joint is set at its neutral position), and prevent both plantar flexion (the flexion in the direction that the toe drops down) and dorsal flexion (the flexion in the direction that the toe is lifted up) of the ankle joint so that talipes equinus and/or drop foot are corrected.

Therefore, the short leg braces of this type fix the ankle joint relatively firmly, preventing almost any motion of the ankle joint, and thus have a drawback that they cannot allow a patient to walk in a natural and smooth manner.

It might be possible to adjust the above shown conventional short leg brace by selecting the material thereof or by adjusting the width of the junction 51 between the foot mount 10A and the calf splint 20A so as to provide some flexibility to the short leg brace, and therefore it might be possible to change the width of the junction 51 depending on the condition of the patient or on how far the patient's rehabilitation program has proceeded (by scraping the junction 51 so that its width progressively reduces as the rehabilitation program proceeds). However, because it is very difficult to restore the short leg brace if it is reduced excessively, such adjustment is seldom practiced but instead it is common to make the short leg brace anew every several years (under the current Japanese Disabled Persons Welfare Act, it is permitted to remake the short leg brace every three years).

With the ankle joint fixed by a support, it is impossible for a patient to walk in a natural manner. FIG. 6 shows one cycle of walking. The walking cycle can be divided into a stance phase in which a leg of interest (the right leg in FIG. 6) is in contact with the floor and a swing phase in which the leg of interest is apart from the floor. In the drawing, the stance phase is defined as a period between the heel contact (a) and the toe separation (1), while the swing phase is defined as a period between the toe separation (1) and the next heel contact (p).

In this walking cycle, among the ankle joint dorsal flexion muscle (precisely the tibialis anterior, hereinafter referred to as the dorsal flexion muscle) and the ankle joint plantar flexion muscle (precisely the triceps muscle of the calf, hereinafter referred to as the plantar flexion muscle), the one which is shown with a shade in FIG. 6 is the working muscle. In the period from the heel contact (a) to the foot flat (b) at which the whole foot sole comes into contact with the floor, the dorsal flexion muscle works to prevent abrupt drop of the toe. In the period from the foot flat (b) through the heel separation (h) to the toe separation (1), the plantar flexion muscle works to support the weight, move the center of gravity forward, and cause the toe to kick the floor. In the swing phase between the toe separation (1) and the next heel contact (p), the dorsal flexion muscle works to lift up the toe so that a clearance is maintained between the foot and the floor. Thus, in the walking action, the plantar and dorsal flexion muscles work alternately so that the ankle repeats the plantar and dorsal flexions.

Referring to FIG. 7, the period between the heel contact (a) and the foot flat (b) is described in more detail in the following. In this drawing, K designates the knee (or the knee joint), W the center of gravity, A the ankle (or the ankle joint), F the foot (or the part lower than the ankle), TH the thigh, and SH the shank. First, the foot F is moved forward and the heel thereof is brought into contact with the floor (this state is shown in the left-side drawings, and designated with HC which is an abbreviation of "heel contact"). Subsequently, as the body moves forward (i.e., the center of gravity moves forward), the foot is, via the state shown in the middle drawings, gradually brought into full contact with the ground until the toe contacts the floor (this state is designated with EF which is an abbreviation of "foot flat").

In the period from HC to FF, a person without a disability can control the plantar flexion of his or her ankle joint as the weight is gradually applied to the foot from the left-side state to the right-side state shown in FIG. 7(A). In other words, the dorsal flexion muscle gradually expands while preventing abrupt drop of the foot toe. As a result, the knee is substantially maintained on the line of action of.the vector representing the reaction force from the floor (the vector represents a resultant of the forces provided from the floor over the whole foot sole when the weight is applied to the foot), which is shown in the drawing by the arrow directed upward from the floor, so that the person can walk smoothly and steadily.

However, the dorsal flexion muscle of a person with hemiplegia may be weakened and the plantar flexion muscle may have an extraordinary tension, always pulling the foot toe in the direction of plantar flexion. As a result, the foot toe comes into contact with the floor immediately after HC, with the knee K positioned on a rear side with respect to the line of action of the vector representing the reaction force from the floor as shown in FIG. 7(B), leading to an overextension of the knee K. To prevent this, the short leg brace is required to have an ability to assist the dorsal flexion muscle while at the same time allowing the plantar flexion during the period from HC to FF.

In the case where the conventional short leg brace of FIG. 5 is used, because the short leg brace fixes the ankle joint in the neutral position, it is necessary to move the whole lower leg forward in order to accomplish the transition from HC to FF, as shown in FIG. 7(C). This causes the knee K to be positioned excessively on the front side of the line of action of the vector representing the reaction force from the floor, creating a problem that the knee K cannot be steadily controlled if the extensor muscle thereof is weak.

After FF in FIG. 7, the portion of the weight applied to the foot is gradually increased, causing the ankle joint A to bend in the direction of dorsal flexion, as shown by the step (c) and its subsequent steps in FIG. 6. In this period, the short leg brace is required to move freely (without a resist) in the direction of dorsal flexion so as not to hinder the natural motion of the ankle joint A. Thus, the short leg brace is required to assist the dorsal flexion muscle in the period from HC to FF ((a)–(b)) and in the swing phase ((l)–(o)) in FIG. 6. The required supplementary torque during the swing phase is very small, because during this period the short leg brace only has to lift up the foot. However, in the period from HC to FF, the required supplementary torque is relatively large because the short leg brace has to prevent abrupt drop of the foot toe against the weight increasingly applied to the foot. Thus, if the short leg brace can produce an adequate supplementary torque in this period, it will improve the user's walk over the whole walking cycle including the period after FF.

Examples of the prior art are disclosed in the specifications of Japanese Patent Publication No.61-16173 and Japanese Utility Model Publication No.61-43473.

The embodiment of No.61-16173 comprises a supporting member which extends from the foot sole to an upper part of the Achilles tendon via an outer side of the ankle. The supporting member can be secured to the leg by straps. Further, a calf splint is hinged to an upper end portion of the supporting member, and tension springs are used to urge the toe side portion toward the hinge between the supporting member and the calf splint.

However, this conventional embodiment essentially fixes the ankle joint by means of the supporting member, and the resultant essentially limited movement of the ankle joint is elastically hindered by the tension springs. Therefore, the degree of assistance to the dorsal flexion muscle and the allowable range of the plantar flexion are both quite limited and insufficient to achieve natural movement of the ankle joint.

The embodiment of No.61-43473 is provided with a large flexibility (in other words, cat be bent with a small force) as a result of greatly reducing the width of the joint 51 of the embodiment shown in FIG. 5, while a side strut having an S-shape so as to function as a spring is provided in a manner that it extends upright with its upper end vertically slideably engaged to the calf splint 20a.

In this way, with proper provision of a stopper for limiting the vertical sliding movement of the side strut, it is possible to generate a large resisting force against the plantar flexion while allowing substantially free dorsal flexion, so that an advantageous short leg brace is achieved. However, as the side strut is stretched or compressed, its degree of flexion changes and the side strut can engage and irritate the skin of the leg, creating a problem that this embodiment is not suitable for a long hour walking.

In view of such problems of the prior art, a primary object of the present invention is to provide a short leg brace which can assist the patient in achieving more natural walking. It is also contemplated that the present invention can be used in an adaptability test conducted to find a suitable supplementary torque for each patient with hemiplegia, in which the patient's walking condition is examined for various magnitudes of supplementary torque.

DISCLOSURE OF THE INVENTION

To achieve the above objects, the present invention provides a short leg brace comprising: a foot mount 10 for supporting a foot sole S; and a calf splint 20 to be set along a calf C, the foot mount 10 and the calf splint 20 being pivotably attached to each other by a pivot 40 at an ankle portion A so as to allow plantar and dorsal flexions; wherein a compression spring 31 is provided between the calf splint 20 and a heel portion H of the foot mount 10 so as to elastically hinder the plantar flexion of the foot mount 10.

Thus the compression spring 31 elastically hinders the plantar flexion of the foot mount 10 around the pivot 40, in other words, the compression spring 31 functions to assist the ankle joint dorsal flexion muscle during the period from HC to FF.

According to another aspect of the present invention, a short leg brace is provided which comprises: a foot mount 10 for supporting a foot sole S; and a calf splint 20 to be set along a calf C, the foot mount 10 and the calf splint 20 being pivotably attached to each other by a pivot 40 at an ankle portion A so as to allow plantar and dorsal flexions; wherein a compression spring 31 is provided between the calf splint 20 and a heel portion H of the foot mount 10 so as to elastically hinder the plantar flexion of the foot mount 10 with a torque greater than or equal to 5 Nm and less than or equal to 20 Nm for 10 degree plantar flexion angle of the foot mount 10.

A suitable magnitude of the supplementary torque is determined depending on various factors such as the degree of disability, muscle strength, age, sex, weight, etc. of each patient. Besides, the suitable magnitude of the supplementary torque may change as the rehabilitation program proceeds. Numerous actual tests of the short leg brace have shown that it is preferable that the supplementary torque for the 10 degree plantar flexion angle of the ankle joint is adjustable within a range from 5 to 20 Nm. Thus, by using the compression spring 31 which is capable of elastically hindering the plantar flexion with a torque of 5–20 Nm for the 10 degree plantar flexion angle, it is possible to achieve a short leg brace which is simple and compact, but is capable of providing an adequate supplementary torque.

According to yet another aspect of the present invention, a short leg brace is provided which comprises: a foot mount 10 for supporting a foot sole S; and a calf splint 20 to be set along a calf C, the foot mount 10 and the calf splint 20 being pivotably attached to each other by a pivot 40 at an ankle portion A so as to allow plantar and dorsal flexions; wherein the short leg brace further comprises: a spring housing 30 which has an upper end connected to the calf splint 20 and in which are accommodated a compression spring 31 and a slider 32, the slider 32 having a lower portion projecting out through a lower end of the spring housing 30 and being moveable within the spring housing 30 so as to be capable of compressing the compression spring 31; and a telescopic shaft 33 which is passed through the slider 32 so as to be slideable in the slider 32 and which has in its lower portion a stopper part 33a adapted to abut an outer surface of the slider 32, with a lower end of the telescopic shaft 33 connected to a rear side of a heel portion H of the foot mount 10.

In this way, when the foot mount 10 is moved in the direction of plantar flexion, the telescopic shaft 33 is pushed deeper into the spring housing 30, and after the stopper part 33a abuts the slider 32, the compression spring 31 is compressed to generate a force for assisting the ankle joint dorsal flexion muscle. On the other hand, when the foot mount 10 is moved in the direction of dorsal flexion, the telescopic shaft 33 freely travels without engaging the compression spring 31 and therefore without hindering the dorsal flexion. Since the sliding movement of the telescopic shaft 33 is guided by an inner surface of the slider 32 which can be formed in a relatively elongate shape, high structural strength is achieved. In stead of the combination of the telescopic shaft and the slider as shown above, it may be possible to integrally form the telescopic shaft and the slider, use one or plurality of springs having a non-linear compression profile in that the reaction force generated by the springs abruptly increases from a certain point, and set the slider in the spring housing 30 so that in the neutral position the slider slightly pushes the springs. In this way also, similar effects to those of the above embodiment can be obtained, or it may be possible to allow the ankle joint to move freely in the direction of dorsal flexion while elastically hindering the plantar flexion beyond a prescribed angle, except that some elastic force is applied to the ankle joint in its neutral position.

According to yet another aspect of the present invention, a short leg brace is provided which comprises: a foot mount 10 for supporting a foot sole S; and a calf splint 20 to be set along a calf C, the foot mount 10 and the calf splint 20 being pivotably attached to each other with a pivot 40 at an ankle portion A so as to allow plantar and dorsal flexions; wherein the short leg brace further comprises: an upper bracket 34 secured to the calf splint 20; an attachment piece 34b pivotably connected to the upper bracket 34 around a horizontal axis 34a extending in a lateral direction with respect to the foot; a threaded rod member 35 engaged to a lower end of the attachment piece 34b in such a manner that its position relative to the attachment piece 34b is adjustable; a spring housing 30 engaged by the threaded rod member 35, the spring housing containing therein a compression spring 31 and a slider 32, the slider 32 having a lower portion projecting out through a lower end of the spring housing 30 and being moveable within the spring housing 30 so as to be capable of compressing the compression spring 31; a telescopic shaft 33 which is passed through the slider 32 so as to be slideable in the slider 32 and is provided in its lower portion with a stopper part 33a adapted to abut an outer surface of the slider 32; and a lower bracket 36 which is pivotably connected to a lower end of the telescopic shaft 33 around a horizontal axis 36a extending in a lateral direction with respect to the foot and which is secured to a rear side of a heel portion H of the foot mount 10.

In this way, by changing the position of the threaded rod member 35 relative to the attachment piece 34b, it is possible to adjust the point where the compression spring begins to be compressed as a result of the plantar flexion. Specifically, when the threaded rod member 35 has been screwed deep into the attachment piece 34b, a large plantar flexion angle of the ankle joint is required to begin to compress the compression spring 31, while when the threaded rod member 35 has been screwed less deep into the attachment piece 34b so that the distance between the spring housing 30 and the attachment piece 34b has become relatively large, the compression spring 31 begins to be compressed with a relatively small plantar flexion angle.

Thus, the short leg brace according to the present invention can enable a patient to walk smoothly by assisting the dorsal flexion muscle with the compression spring 31 while allowing the plantar and dorsal flexions of the ankle joint.

Since the compression spring 31 is easily replaceable, the torque A provided from the short leg brace to assist the dorsal flexion can be adjusted so that it suits to a condition of each patient.

By setting the supplementary torque from the compression spring 31 within a range from 5 Nm to 20 Nm, it is possible to achieve such an assistance to the dorsal flexion muscle as was not contemplated in the prior art.

By utilizing the spring housing 30, compression spring 31, slider 32 and telescopic shaft 33, with the upper end of the spring housing 30 connected to the calf splint 20 and the lower end of the telescopic shaft 33 connected to the foot mount 10, a short leg brace is provided in which the movement of the foot mount 10 in the direction of dorsal flexion is not hindered by the compression spring 31.

The structure in which the threaded rod member 35 is engaged to the lower end of the attachment piece 34b in such a manner that its position relative to the attachment piece 34b is adjustable and the spring housing 30 meshes with the threaded rod member 35 allows adjustment of the ankle joint angle at which the compression spring 31 begins to be compressed, and accordingly the ankle joint angle at which the supplementary torque begins to be generated can be suitably set for each patient.

Other features. and objects of the present invention will be apparent from the following description taken in connection with the accompanying drawings.

BEST MODE FOR CARRYING OUT THE INVENTION

Figure 1:
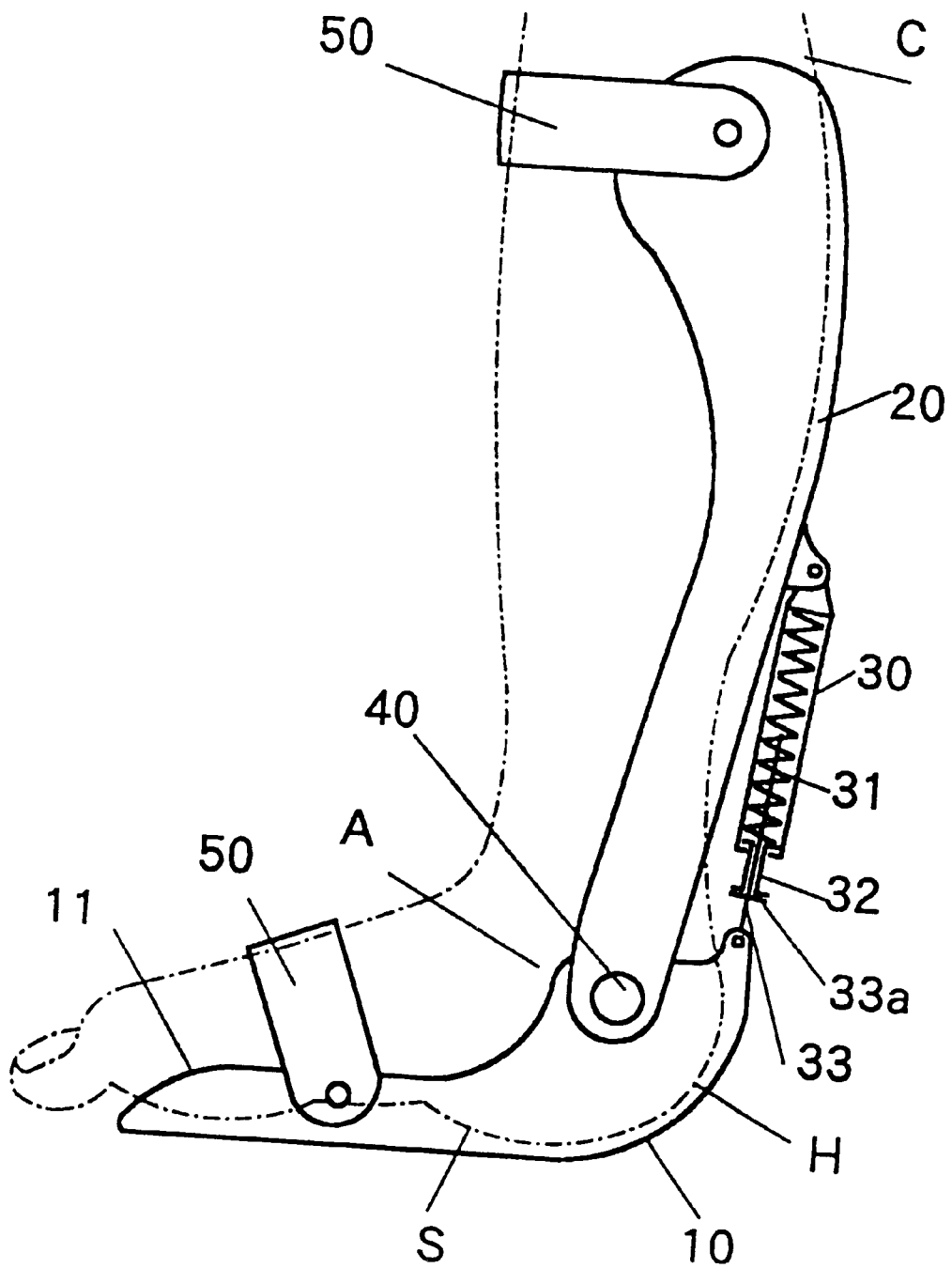
FIG. 1 is a frontal view showing one embodiment of the present invention.

In the following, embodiments of the present invention are described with reference to the accompanied drawings. The numeral reference 10 denotes a foot mount, and the numeral reference 20 denotes a calf splint. The foot mount 10 is made of a relatively rigid synthetic resin material and supports the foot sole S (as well as the heel H). The foot mount 10 comprises a flat portion somewhat larger than the foot sole and a pair of upright side walls 11, 11 so that the foot mount 10 cannot be deformed easily.

The calf splint 20 is also made of a relatively rigid synthetic resin material and has a generally trough-like shape adapted for being set along the calf C. As in the conventional embodiment, the calf splint 20 and the foot mount 10 can be secured to the leg with fixing bands 50, 50 or the like.

The foot mount 10 and the calf splint 20 are pivotably attached to each other by pivots 40 at an ankle portion A so as to allow plantar and dorsal flexions. Although not shown in the drawings, the pivots 40 are provided on opposite lateral sides of the foot so that they do not engage the somewhat protruding ankle portion A of the patient when the short leg brace is fitted to the patient.

The short leg brace further comprises a compression spring 31 disposed between the calf splint 20 and the foot mount 10 in order to elastically hinder the plantar flexion of the foot mount 10.

The compression spring 31 for elastically hindering the plantar flexion works to assist the dorsal flexion muscle. To the calf splint 20 is pivoted an upper end of a spring housing 30 elongating in a generally vertical direction as shown in FIG. 1, and the compression spring 31 is accommodated in an upper part of the spring housing 30. Under the compression spring 31 in the spring housing 30 is accommodated a slider 32 such that the slider 32 can slide inside the spring housing 30 to compress the compression spring 31. The lower portion of the slider 32 projects out of the spring housing 30. Further, a shaft 33 whose lower end is pivotably connected to the heel portion of the foot mount 10 extends through the slider 32. The shaft 33 has a stopper part 33a adapted to abut the lower end of the slider 32. In this way, when the foot mount 10 moves in the direction of plantar flexion and the shaft 33 travels upward, the stopper part 33a pushes the slider 32 upward, which in turn compresses the compression spring 31. On the other hand, when the foot mount 10 moves in the direction of dorsal flexion from the state shown in FIG. 1, the shaft 33 freely travels downwardly without any interaction with the compression spring 31. To prevent the compression spring 31 from pushing out the slider 32 from the spring housing 30, the outer diameter of the portion of the slider 32 contained inside the spring housing 30 is larger than that of the opening formed in the lower end of the spring housing 30.

Thus, when the foot mount 10 rotates around the pivot axis 40 in the direction of plantar flexion with its toe side portion moving downwardly from the state shown in FIG. 1, the shaft 33 is caused to move upwardly together with its stopper part 33a and pushes the slider 32 so as to compress the compression spring 31. The force (not shown in the drawing) generated by the compression spring 31 when the spring 31 is compressed as a result of the plantar flexion of the ankle joint fitted with the short leg brace of the present invention works as a resisting force against the plantar flexion, in other words, the compression spring 31 provides a force urging the heel portion H of the foot mount 10 in the downward direction or provides a supplementary torque to the dorsal flexion muscle.

Figure 5:
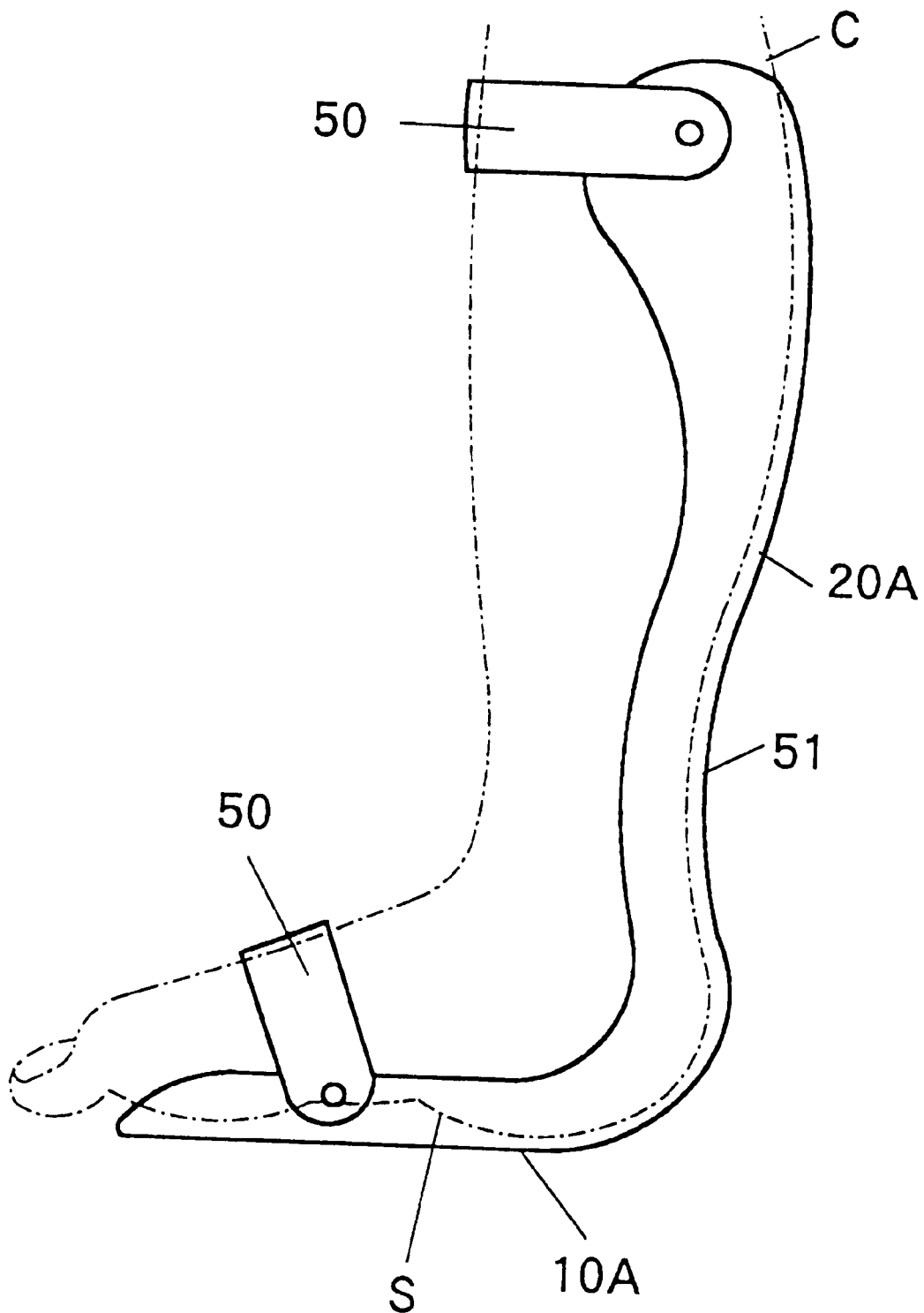
FIG. 5 is a frontal view of a conventional embodiment.
Figure 6:
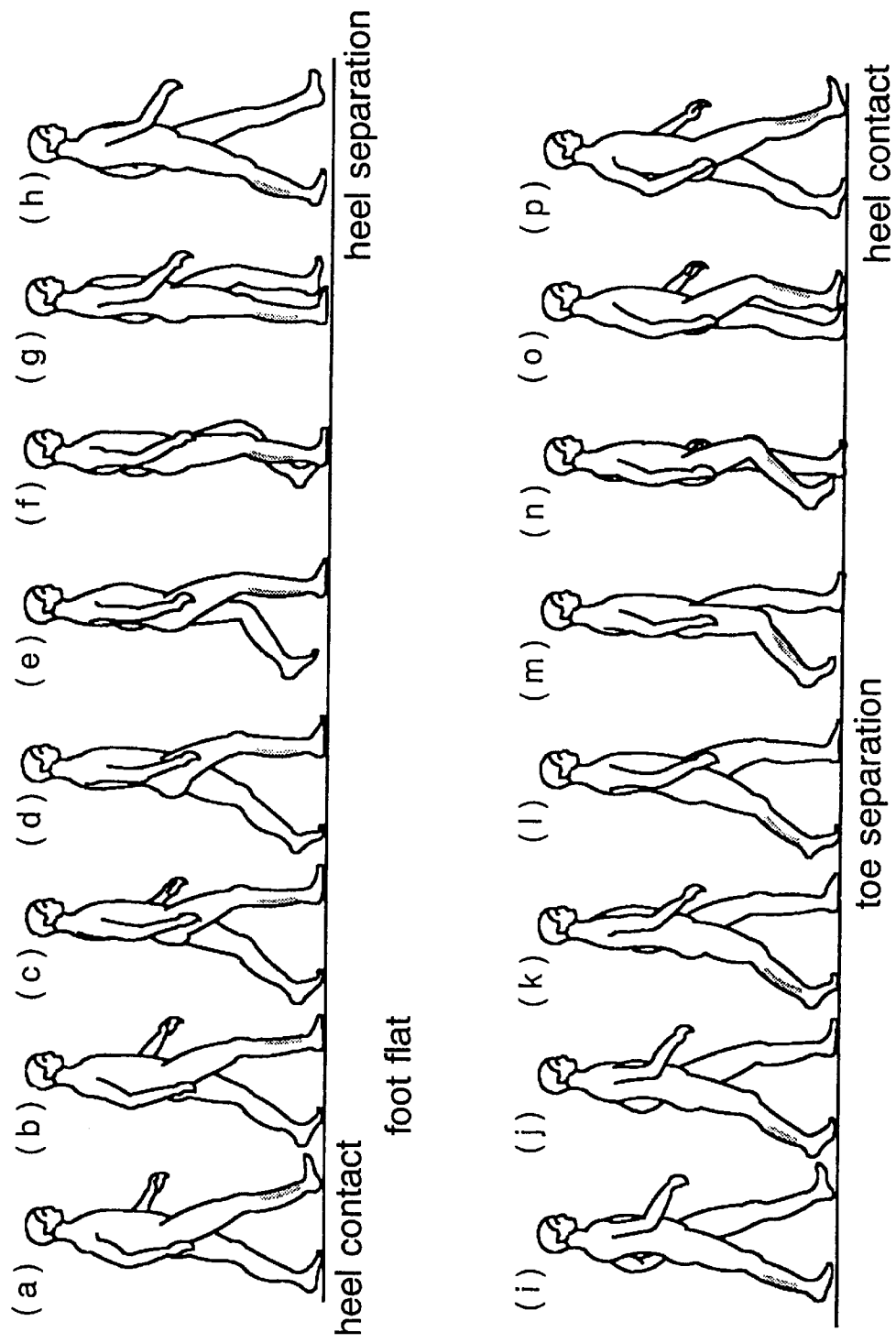
FIG. 6 is a schematic diagram for explaining a walling cycle.
Figure 7:
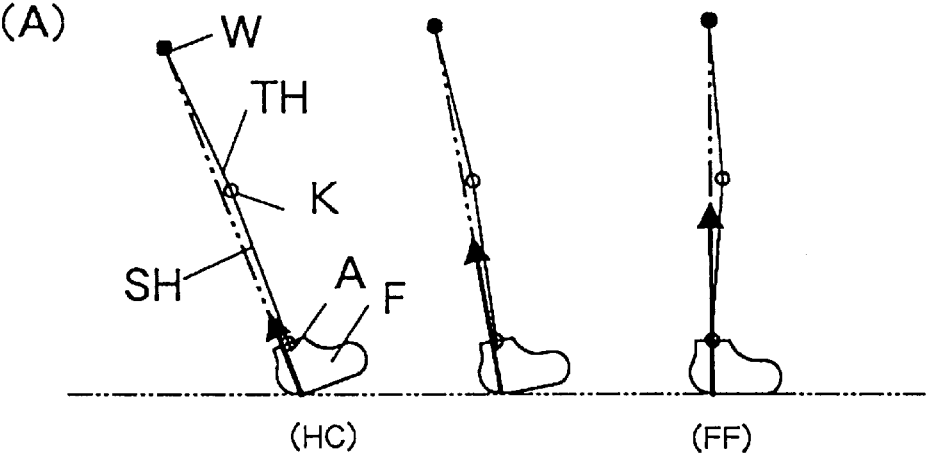
FIG. 7 is a schematic diagram for explaining a part of the waling cycle.
Figure 7:
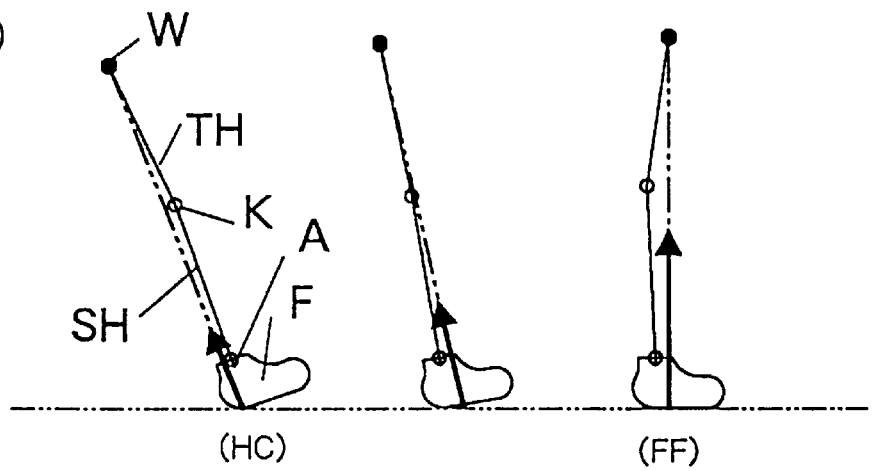
Figure 7:
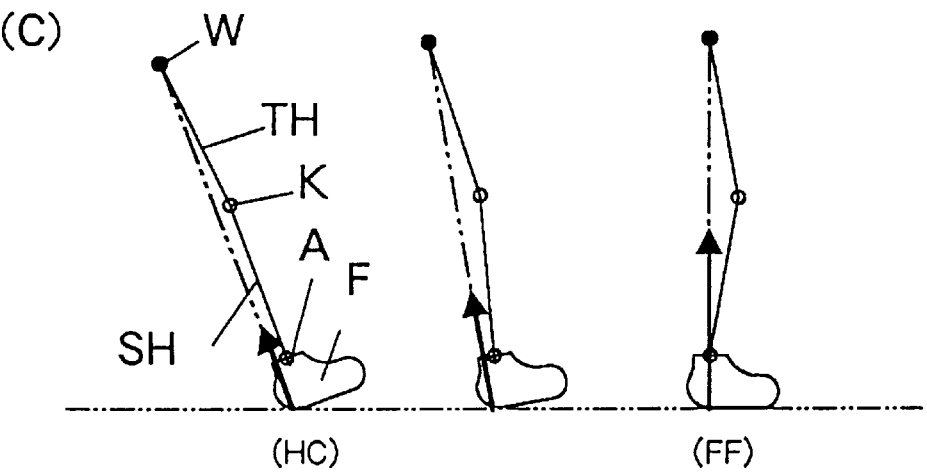

Conventionally, because it was customary to fix the ankle joint in a manner such as shown in FIG. 5, the magnitude of supplementary torque required for assisting the dorsal flexion muscle had not been studied sufficiently, and no concrete values thereof had been obtained. Thus, numerous actual tests of the short leg brace were conducted to show that a supplementary torque of 5–20 Nm was necessary for the foot mount 10's plantar flexion angle of 10 degrees. Therefore, in order to achieve such a supplementary torque for assisting the dorsal flexion muscle, it is preferred to use a compression spring which can elastically hinder the 10 degree plantar flexion of the foot mount 10 with a torque greater than or equal to 5 Nm and less than or equal to 20 Nm as the above compression spring 31.

If one end of the compression spring 31 were connected to the foot mount 10 and the other end thereof to the calf splint 20, the compression spring 31 would also function as a tension spring. However, as mentioned above, in the walking cycle the ankle joint needs to move in the direction of dorsal flexion preferably without any resisting force generated from the spring. In order to prevent the spring from hindering the dorsal flexion, in the embodiments shown in FIGS. 1 and 2, the spring housing 30 has an upper end connected to the calf splint 20; the compression spring 31 and the slider 32 are accommodated in the spring housing 30, the slider 32 having a lower portion projecting out through a lower end of the spring housing 30 and being moveable within the spring housing 30 so as to be capable of compressing the compression spring 31; and a telescopic shaft 33 having in its lower portion a stopper part 33a adapted to abut an outer surface of the slider 32 is passed through the slider 32 so as to be slideable in the slider 32, with a lower end of the telescopic shaft 33 connected to a rear side of a heel portion of the foot mount 10.

Figure 2:
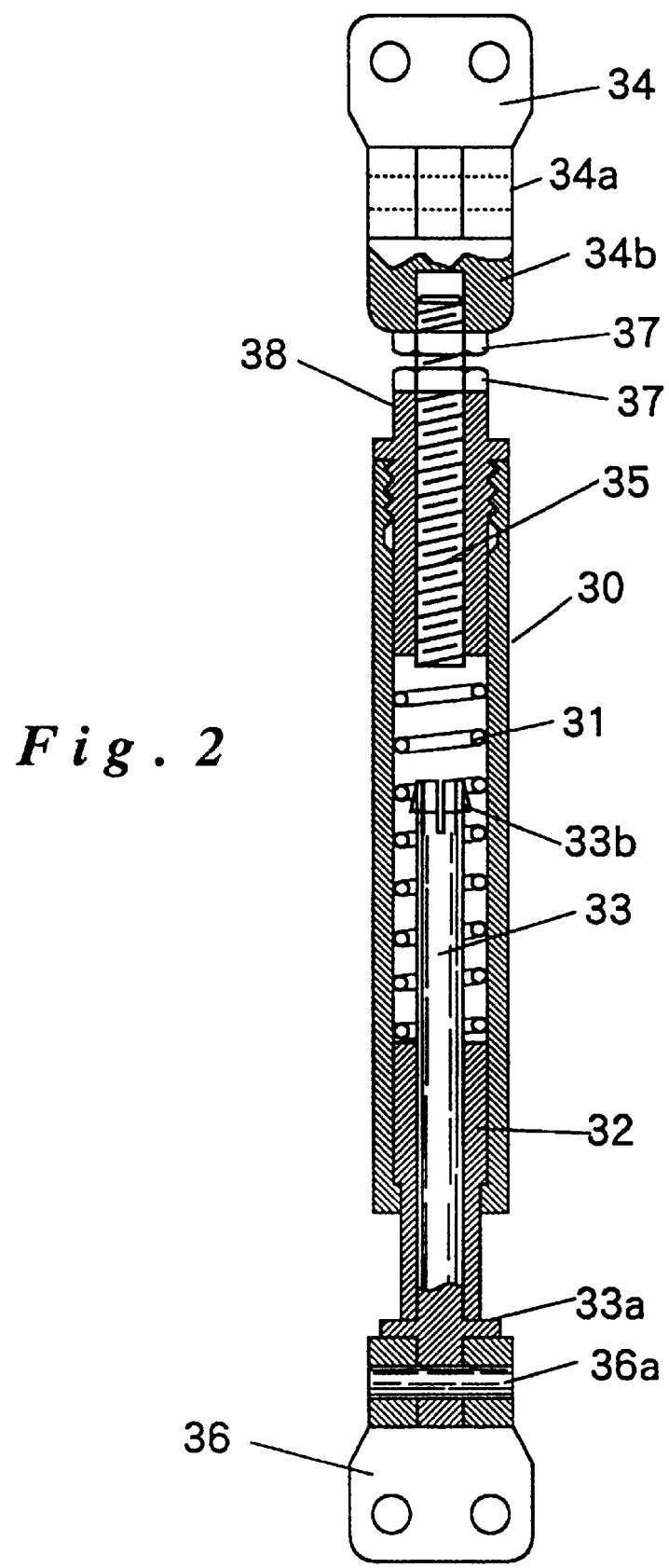
FIG. 2 is a longitudinal cross sectional view of a spring housing used in another embodiment.
Figure 3:
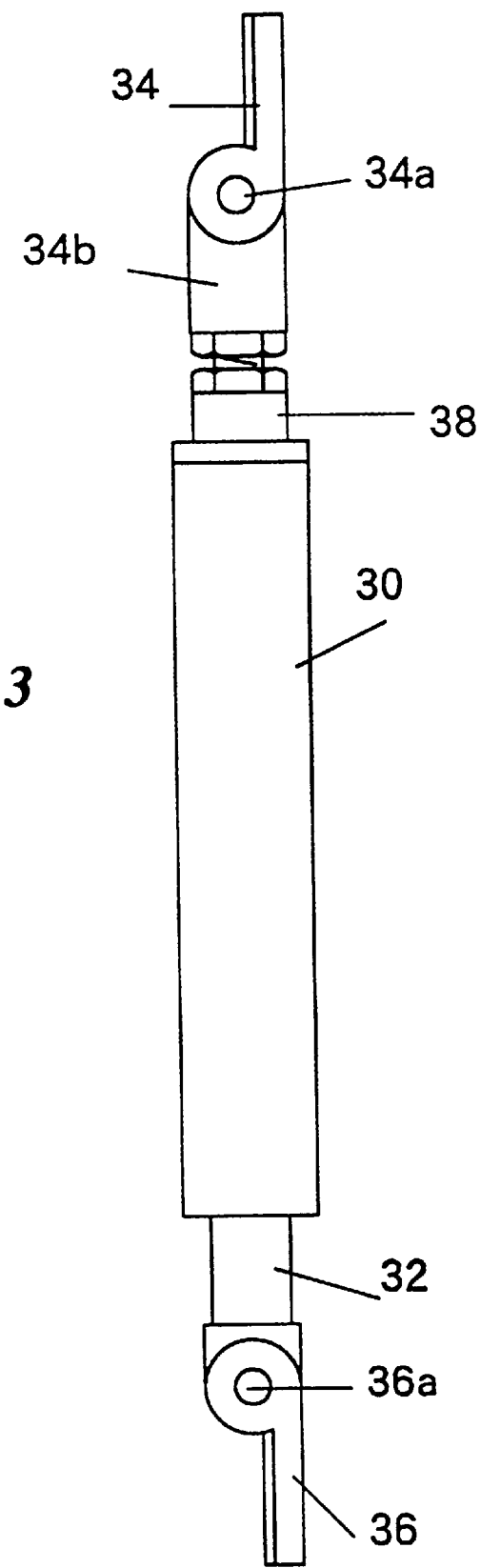
FIG. 3 is a side view of the spring housing.

Thus, if the telescopic shaft 33 in the state shown in FIG. 2 is provided with a force urging it deeper into the spring housing 30 (a force which is directed upwardly with respect to the drawing and which is caused as a result of the plantar flexion), the compression spring 31 is compressed. On the other hand, if a force urging the telescopic shaft 33 toward outside the spring housing 30 (a force which is directed downwardly with respect to the drawing and which is caused as a result of the dorsal flexion) is applied to the telescopic shaft 33 in the state shown in FIG. 2, the telescopic shaft merely travels outward without interaction with the compression spring 31.

In order to prevent the telescopic shaft 33 from dropping off from the spring housing 30, a stopper 33b is formed such that when the shaft 33 is withdrawn from the housing 30 to a predetermined extent, the stopper 33b abuts an upper end of the slider 32 to prevent further withdrawal of the shaft 33. The stopper 33b is formed in a shape of an arrowhead having a longitudinal slit so that the telescopic shaft 33 can be inserted through a central longitudinal bore of the slider 32 but once inserted cannot be removed with an ordinary force.

As describe above, the supplementary torque for assisting the dorsal flexion muscle was measured in numerous actual tests as being in the range of 5–20 Nm, and therefore it is preferred that the toque is adjustable within such a range.

Thus, a short leg brace is provided which comprises: an upper bracket 34 secured to the calf splint 20; an attachment piece 34b pivotably connected to the upper bracket 34 around a horizontal axis 34a extending in a lateral direction with respect to the foot; a threaded rod member 35 engaged to a lower end of the attachment piece 34b in such a manner that its position relative to the attachment piece 34b is adjustable; a spring housing 30 engaged by the threaded rod member 35 so that the rod member 35 can be screwed into and out of the spring housing 30 by turning the rod member 35 relative to the spring housing 30, the spring housing containing therein a compression spring 31 and a slider 32, the slider 32 having a lower portion projecting out through a lower end of the spring housing 30 and being moveable within the spring housing 30 so as to be capable of compressing the compression spring 31; a telescopic shaft 33 which is passed through the slider 32 so as to be slideable in the slider 32 and is provided in its lower portion with a stopper part 33a adapted to abut an outer surface of the slider 32; and a lower bracket 36 which is pivotably connected to a lower end of the telescopic shaft 33 around a horizontal axis 36a extending in a lateral direction with respect to the foot and which is secured to a rear side of a heel portion H of the foot mount 10.

The upper bracket 34 is secured to the calf splint 20, while the lower bracket 36 is secured to the foot mount 10. The horizontal axes 34a and 36a are provided so that the plantar and dorsal flexions are not prevented by connecting the calf splint 20 and the foot mount 10 to each other at positions other than the pivot 40.

The structure in that the threaded rod member 35 is engaged to the lower end of the attachment piece 34b in such a manner that its position relative to the attachment piece 34b is adjustable makes it possible to change the position of the spring housing 30, and thereby adjust the position at which the compression spring 31 begins to be compressed by the plantar flexion. Specifically, if the threaded rod member 35 is secured at a higher position than that shown in FIG. 2, the position at which the upwardly traveling telescopic shaft 33 begins to compress the compression spring 31 also becomes higher. Thus, by changing the position of the spring housing 30 it is possible to adjust the angle of the ankle joint at which the supplementary torque begins to be exerted.

Figure 4:
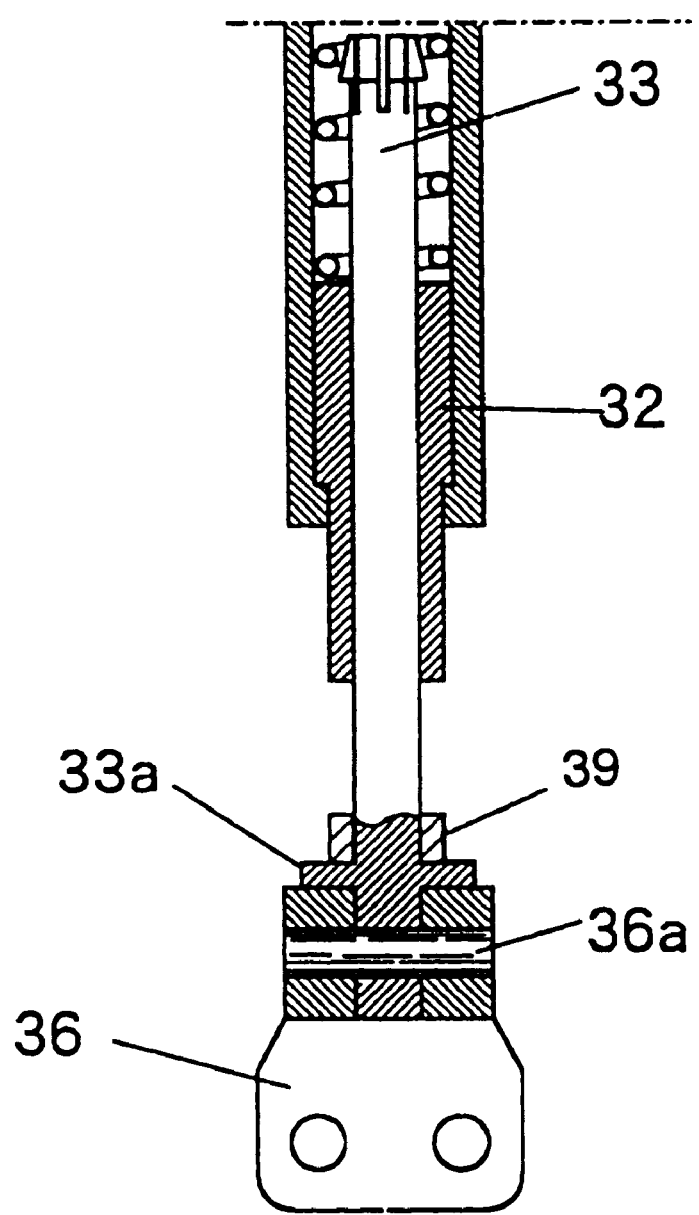
FIG. 4 is a partial longitudinal cross sectional view of a yet another embodiment of a spring housing.

As shown in FIG. 4, a spacer 39 can be fitted on a part of the telescopic shaft 33 between the stopper 33a and the slider 32. The spacer 39 can consist of for example a C-ring having a proper thickness. By suitably selecting the thickness, the angle of the ankle joint at which the supplementary torque begins to be exerted can be adjusted in a similar manner to that described above.

In the embodiment shown in the drawing, the spring housing 30 is engaged by the threaded rod member 35 so that the rod member 35 can be screwed into and out of the spring housing by turning the rod member 35 relative to the spring housing 30. This also allows adjustment of the compression force of the compression spring 31. If the threaded rod member 35 is positioned so that a longer part thereof protrudes over the spring housing 30 than the state shown in FIG. 2, the compression spring is brought into a pre-compressed state with a somewhat reduced total length thereof, requiring a larger force for its further compression, in other words, resulting in a larger supplementary force for assisting the dorsal flexion muscle.

Although the spring force generated by the compression spring 31 is adjustable, it may be difficult in practice to adjust the spring force within the above mentioned range of 5–20 Nm. In such a case, a plurality of compression springs 31 which have different characteristics and which can be replaceable with each other may facilitate achieving a suitable supplementary torque for assisting the dorsal flexion muscle.

In the drawing, the reference numerals 37, 37 denote securing nuts, while the reference numeral 38 denotes a component part for receiving the threaded rod member.

Although the present invention has been described as a short leg brace, the present invention can be used in determining an optimum magnitude of supplementary torque for each patient. In such a case, the short leg brace is temporarily fitted on the patient and then the patient's walking condition is examined. By using the test results, a short leg brace whether according to the present invention or of the prior art can be manufactured more efficiently.

Although the present invention has been described in terms of preferred embodiments thereof, it is obvious to a person skilled in the art that various alterations and modifications are possible without departing from the scope of the present invention. For example, instead of the compression spring, any elastic member such as a torsion spring or a tension spring can be used to embody the present invention.

What we claimed is:

1. A short leg brace, comprising:
   a foot mount (10) for supporting a foot sole (S); and
   a calf splint (20) to be set along a calf (C), the foot mount (10) and the calf splint (20) being pivotably attached to each other by a pivot (40) at an ankle portion (A) so as to allow plantar and dosal flexions;
   wherein an elastic member assembly is provided between the calf splint (20) and a heel portion (H) of the foot mount (10), elastic member assembly comprising:
   a first portion having at its one end a pivot part which is pivotably connected to one of the calf splint (20) or a heel portion (H) of the foot mount (10);
   a second portion having at its one end a pivot part which is pivotably connected to the other one of the calf splint (20) or the heel portion (H) of the foot mount (10); and
   a compression spring (31) disposed between the first and second portion;
   the first portion and the second portion being engaged so that they can move toward and away from each other;
   whereby the elastic member assembly applies such an elastic force to the foot mount (10) as to urge the same in a direction of the dorsal flexion thereof when an ankle joint is on a plater flexion side with respect to a prescribed ankle joint angle while applying substantially no elastic force to the foot mount (10) when the ankle joint is on a dorsal flexion side with respect to the prescribed ankle joint angle during use.

2. A short leg brace according to claim 1, wherein the first portion compression a spring housing (30) for accommodating the compression spring (31); and
   the second portion comprises:
   a slider (32) slideably disposed in the spring housing (30) so as to compress the compression spring (31), the slider (32) having stopper means for preventing the slider (32) from being released from the spring housing (30) and a bore extending in a direction of the sliding movement; and
   a telescopic shaft (33) slideably received in the bore of the slider (32) and having one end connected to the pivot part of the second portion;
   wherein the slider (32) and the telescopic shaft (33) have respective stopper surfaces which are adapted to abut each other and limit a motion of the telescopic shaft (33) toward inside of the bore of the slider (32) so as to define the prescribed ankle joint angle.

3. A short leg brace according to claim 2, further comprising means (39) for adjusting a distance between the stopper surface of the telescopic shaft (33) and the pivot part of the second portion.

4. A short leg brace according to claim 2, further comprising means for adjusting a distance between the stopper surface of the slider (32) and the pivot part of the first portion in a state that the stopper surface of the slider (32) and the stopper surface of the telescopic shaft (33) do not abut each other.

5. A short leg brace according to claim 1, further comprising means for adjusting the prescribed ankle joint angle.

6. A short leg brace according to claim 1, wherein the elastic member assembly elastically hinders the plantar flexion of the foot mount (10) with a torque greater than or equal to 5 Nm and less than or equal to 20 Nm for 10 degree plantar flexion angle of the foot mount (10).

7. A short leg brace, comprising:
   a foot mount (10) for supporting a foot sole (S); and
   a calf splint (20) to be set along a calf (C), the foot mount (10) and the calf splint (20) being pivotably attached to each other by a pivot (40) at an ankle portion (A) so as to allow plantar and dorsal flexions;
   wherein the short leg brace further comprises: an upper bracket (34) secured to the calf splint (20); an attachment piece (34b) pivotably connected to the upper bracket (34) around a horizontal axis (34a) extending in a lateral direction with respect to the foot; a threaded rod member (35) engaged to a lower end of the attachment piece (34b) in such a manner that its position relative to the attachment piece (34b) is adjustable; a spring housing (30) engaged by the threaded rod member (35), the spring housing containing therein a compression spring (31) and a slider (32), the slider (32)

having a lower portion projecting out through a lower end of the spring housing (30) and being moveable within the spring housing (30) so as to be capable of compressing the compression spring (31); a telescopic shaft (33) which is passed through the slider (32) so as to be slideable in the slider (32) and is provided in its lower portion with a stopper part (33*a*) adapted to abut an outer surface of the slider (32); and a lower bracket (36) which is pivotably connected to a lower end of the telescopic shaft (33) around a horizontal axis (36*a*) extending in a lateral direction with respect to the foot and which is secured to a rear side of a heel portion (H) of the foot mount (10).

* * * * *